United States Patent
Sigurdarson et al.

(10) Patent No.: US 11,648,351 B2
(45) Date of Patent: May 16, 2023

(54) POWER UNIT FOR DRUG DELIVERY DEVICE

(71) Applicant: Novo Nordisk A/S, Bagsvaerd (DK)

(72) Inventors: Noekkvi Steinn Sigurdarson, Koebenhavn (DK); Nicolai Michael Jensen, Koebenhaven (DK)

(73) Assignee: Novo Nordisk A/S, Bagsvaerd (DK)

(*) Notice: Subject to any disclaimer, the term of this patent is extended or adjusted under 35 U.S.C. 154(b) by 569 days.

(21) Appl. No.: 16/765,268

(22) PCT Filed: Nov. 20, 2018

(86) PCT No.: PCT/EP2018/081887
§ 371 (c)(1),
(2) Date: May 19, 2020

(87) PCT Pub. No.: WO2019/097076
PCT Pub. Date: May 23, 2019

(65) Prior Publication Data
US 2020/0368435 A1    Nov. 26, 2020

(30) Foreign Application Priority Data

Nov. 20, 2017 (EP) ..................................... 17202533

(51) Int. Cl.
*A61M 5/20* (2006.01)
*A61M 5/315* (2006.01)
*A61M 5/34* (2006.01)

(52) U.S. Cl.
CPC ...... *A61M 5/2033* (2013.01); *A61M 5/31585* (2013.01); *A61M 5/31593* (2013.01);
(Continued)

(58) Field of Classification Search
CPC ............ A61M 5/2033; A61M 5/31585; A61M 5/348; A61M 5/31533; A61M 5/31525;
(Continued)

(56) References Cited

U.S. PATENT DOCUMENTS 8,702,660 B2    4/2014  Karlsson
10,004,852 B2*  6/2018  Marsh ................. A61M 5/3155
(Continued)

FOREIGN PATENT DOCUMENTS

CN    103547304 A    1/2014
CN    106215284 A    12/2016
(Continued)

*Primary Examiner* — Nathan R Price
*Assistant Examiner* — Tania Ismail
(74) *Attorney, Agent, or Firm* — Wesley Nicolas

(57) ABSTRACT

The present invention provides a power unit (1) for a drug delivery device as well as methods for providing and mounting the power unit (1) in the drug delivery device. The power unit (1) comprises a first interface member (30) extending along a reference axis and comprising a hollow body (31) and a first engagement structure (35), a second interface member (10) comprising a tubular structure (11) extending at least partially through the hollow body (31) and having a skirt (12), and a second engagement structure (14) configured for releasable engagement with the first engagement structure (35), and a torsion spring (20) comprising a first end portion (23) being attached to the first interface member (30) and a second end portion (22) being attached to the second interface member (10), the torsion spring (20) being pre-strained to induce a relative rotational motion between the first interface member (30) and the second interface member (10). The first interface member (30) and the second interface member (10) are configured for relative motion along the reference axis from a first relative axial position in which the first engagement structure (35) and the second engagement structure (14) are engaged to prevent the rela- (Continued)

tive rotational motion between the first interface member (30) and the second interface member (10) to a second relative axial position in which the first engagement structure (35) and the second engagement structure (14) are disengaged. In the first relative axial position of the first interface member (30) and the second interface member (10) the torsion spring (20) is accommodated in a user inaccessible space (39) defined by the hollow body (31) and the skirt (12).

15 Claims, 4 Drawing Sheets

(52) U.S. Cl.
CPC .......... *A61M 5/348* (2013.01); *A61M 5/31525* (2013.01); *A61M 5/31533* (2013.01); *A61M 5/31565* (2013.01); *A61M 5/31576* (2013.01); *A61M 2005/2013* (2013.01); *A61M 2005/31588* (2013.01)

(58) Field of Classification Search
CPC .......... A61M 5/31565; A61M 5/31576; A61M 2005/2013
See application file for complete search history.

(56) References Cited

U.S. PATENT DOCUMENTS

| 2006/0287630 | A1 | 12/2006 | Hommann |
| 2014/0107587 | A1 | 4/2014 | Hogdahl |
| 2016/0045669 | A1 | 2/2016 | Bayer et al. |

FOREIGN PATENT DOCUMENTS

| WO | 2006126902 A1 | 11/2006 |
| WO | 2011101375 | 8/2011 |
| WO | 2014170177 | 10/2014 |
| WO | 2016001300 | 1/2016 |
| WO | 2017055492 | 4/2017 |
| WO | 2018046733 | 3/2018 |

\* cited by examiner

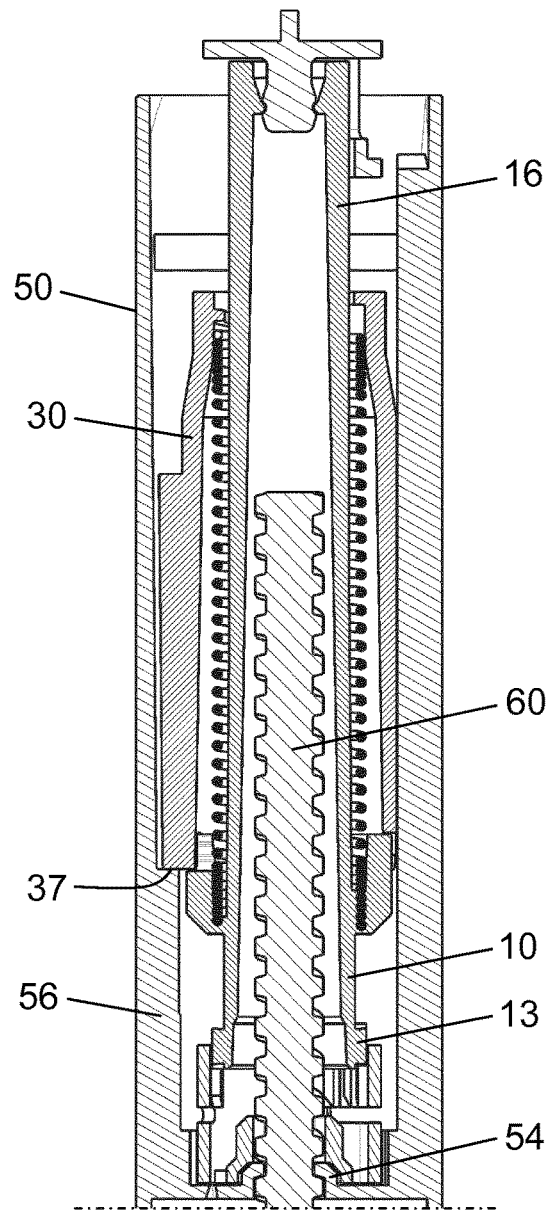
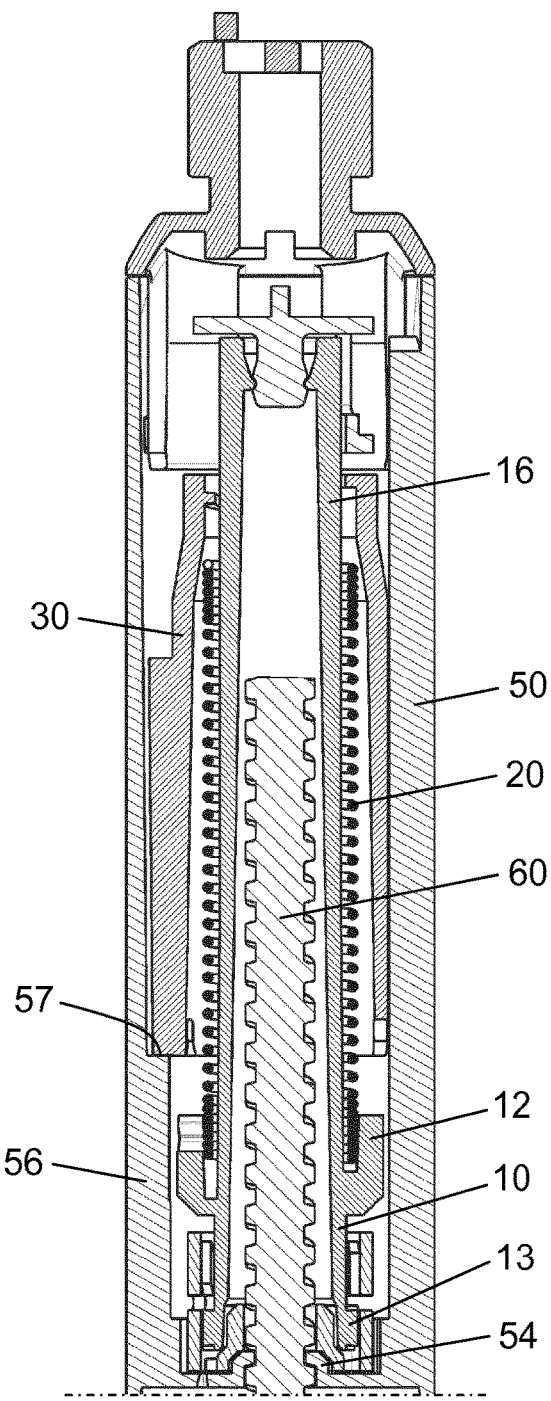
Fig. 5
Fig. 6

POWER UNIT FOR DRUG DELIVERY DEVICE

CROSS-REFERENCE TO RELATED APPLICATIONS

This application is a 35 U.S.C. § 371 National Stage application of International Application PCT/EP2018/081887 (published as WO 2019/097076), filed Nov. 20, 2018, which claims priority to European Patent Application 17202533.0, filed Nov. 20, 2017; the contents of which are incorporated herein by reference.

FIELD OF THE INVENTION

The present invention relates generally to drug delivery devices and more specifically to automatic such devices utilising spring power to actuate a dose expelling mechanism.

BACKGROUND OF THE INVENTION

Automatic drug delivery devices are characterised by having an integrated energy source which is releasable to occasion an expelling of the drug. Many automatic injection devices employ a spring as the energy source because a spring is relatively inexpensive. However, due to friction in the dose expelling mechanism the spring must be pre-strained during manufacturing of the injection device to ensure that sufficient energy is available to deliver an entire expected dose, regardless of its size. This means that the spring is strained such that it applies a certain force or torque even in the "zero" position of the dose setting mechanism, i.e. where a dose has not yet been selected or readied.

The spring pre-straining process is highly sensitive and often results in discarding of parts. One main problem is to strain the spring while maintaining the respective positions of each and every other related component in the device, i.e. components to be driven by the spring or influenced by a release of the spring. The pre-straining is typically carried out by firstly fixating one end of the spring in the device housing and subsequently displacing the other end of the spring relative to the housing and locking the displaced end in position. This requires some rather complex assembly steps, including steps that are carried out in a small internal space of the housing where visual access is limited.

For dose expelling some devices utilise a torsion spring to provide a drive torque to cause rotation of a piston rod threadedly engaged with the device housing. The spring ends are normally provided with hooks, legs or similar means for attachment to neighbouring parts. Such attachment features are cost-raising and in fact account for up to 40% of the total cost of a torsion spring. Furthermore, the attachment features tend to tangle with other parts as well as with the assembly equipment, often causing undesired downtime in assembly lines.

WO 2014/170177 (Novo Nordisk A/S) discloses a torsion spring manufactured without hooked ends and a method of fixating the torsion spring in a medical injection device. By implementing such a solution the total cost of an automatic injection device can be reduced. However, the solution does not markedly improve the issue regarding lack of visual access in the spring pre-straining process. In addition, if the injection device is designed to avoid the need for priming air-shots a zero-point adjustment of the dose expelling mechanism must be carried out to establish proper initial alignment between the piston and the piston rod. This requires physical access to the piston rod which is difficult to obtain with a spring already in place. On the other hand it is difficult to mount the spring without affecting the position of the piston rod, practically rendering an antecedent zero-point adjustment useless.

SUMMARY OF THE INVENTION

It is an object of the invention to eliminate or reduce at least one drawback of the prior art, or to provide a useful alternative to prior art solutions.

In particular, it is an object of the invention to provide a solution for installing a torsion spring in a drug delivery device which is cost-effective and easy to implement.

It is also an object of the invention to provide a solution for installing a torsion spring in a drug delivery device which reduces the complexity of the device assembly process.

It is a further object of the invention to provide such a solution which enables a safe and reliable handling of the torsion spring in the device assembly process.

It is a further object of the invention to provide a cost-effective drug delivery device utilising a torsion spring based drive arrangement.

It is an even further object of the invention to provide a cost-effective torsion spring based drive arrangement for a dual reservoir type of drug delivery device.

In the disclosure of the present invention, aspects and embodiments will be described which will address one or more of the above objects and/or which will address objects apparent from the following text.

A solution embodying the principles of the invention provides a sub-assembly which comprises a first interface member having a first engagement structure, a second interface member having a second engagement structure, and a torsion spring being attached to the first interface member and the second interface member and pre-strained to provide a rotational bias between the two. The first interface member and the second interface member are arranged to enable relative motion along a general, or reference, axis from a first relative axial position in which the first engagement structure and the second engagement structure are engaged so as to prevent relative rotational motion between the first interface member and the second interface member to a second relative axial position in which the first engagement structure and the second engagement structure are disengaged, thereby allowing relative rotational motion between the first interface member and the second interface member. In essence, a power unit is thereby provided which is mountable in a drug delivery device housing and releasable to energise e.g. a dose expelling mechanism. In fact, the power unit may even become part of the dose expelling mechanism.

The sub-assembly provides for a noticeably improved device assembly process in that it allows the torsion spring to be pre-strained outside the device housing and subsequently mounted into the housing while in the pre-strained state. The pre-straining is thus shifted to an ex housing process and may be carried out with adequate visual access to all steps by rotationally fixating a first end portion of the torsion spring to the first interface member, e.g. using the method described in WO 2014/170177, rotationally fixating a second end portion of the torsion spring to the second interface member, e.g. using the method described in WO 2014/170177, inducing a relative rotational motion between the first interface member and the second interface member to bring the first interface member and the second interface member from a first relative angular position to a second relative angular position and thereby rotationally strain the torsion spring, and finally securing the first interface member and the second interface member in the second relative angular position by bringing the first interface member and the second interface member into the first relative axial position.

The sub-assembly further allows for a zero-point adjustment to be concluded prior to installation of the torsion spring in the injection device, as the entire sub-assembly, including the pre-strained spring, may be mounted without contacting the piston rod. For example, if the first interface member and the second interface member are both hollow and the torsion spring is arranged between them the sub-assembly may simply be slid over the piston rod. Zero-point adjustment is particularly relevant for fixed dose injection devices where each activation of the dose expelling mechanism results in the same axial advancement of the piston rod, and where an air-shot therefore may result in loss of a significant drug volume.

In a first aspect of the invention a solution according to claim 1 is provided.

Hence, a sub-assembly, in the form of a power unit, for insertion into a drug delivery device housing is provided. The power unit comprises a) a first interface member extending along a reference axis and comprising a hollow body and a first engagement structure, b) a second interface member comprising a tubular structure, e.g. having a lumen adapted to accommodate a piston rod, extending at least partially through the hollow body, a skirt formed on, or attached to, the tubular structure, and a second engagement structure configured for releasable engagement with the first engagement structure, and c) a torsion spring comprising a first end portion being attached to the first interface member, e.g. retained within the hollow body, and a second end portion being attached to the second interface member, e.g. retained beneath the skirt. The torsion spring is pre-strained and thus contains energy for inducing a relative rotational motion, about the reference axis, between the first interface member and the second interface member.

The first interface member and the second interface member are configured for, i.e. capable of, relative motion along the reference axis from a first relative axial position to a second relative axial position. In said first relative axial position the first engagement structure and the second engagement structure are engaged, thereby preventing relative rotational motion between the first interface member and the second interface member, and the torsion spring is thus cocked. In said second relative axial position the first engagement structure and the second engagement structure are disengaged, thus no longer preventing the torsion spring from releasing its stored energy.

Further, in the first relative axial position of the first interface member and the second interface member the torsion spring is accommodated in a user inaccessible space defined by the hollow body and the skirt. The torsion spring is thereby protected from outside contact, which substantially lowers the risk of failure during assembly. In particular, the torsion spring may be covered by the hollow body and the skirt and may thereby be completely shielded from the exterior of the first interface member and the second interface member, when the first engagement structure and the second engagement structure are engaged.

The second engagement structure may form part of the skirt, which thereby serves both as an anchor for the torsion spring and as a coupling part for interaction with the first interface member.

In exemplary embodiments of the invention the torsion spring extends along the reference axis about a section of the second interface member. This provides for a particularly compact construction of the power unit.

In addition to preventing relative rotational motion between the first interface member and the second interface member the first engagement structure and the second engagement structure may further be configured to obstruct relative axial motion between the first interface member and the second interface member. This means that when the first engagement structure and the second engagement structure are engaged a relative axial motion between the first interface member and the second interface member can only occur if an applied force exceeds a threshold value.

The threshold value may in principle be predetermined or arbitrary but the manufacturer may for example choose to configure the first engagement structure and the second engagement structure such that a specific force applicable during assembly of the injection device is needed to induce the relative axial motion between the first interface member and the second interface member. The threshold value may be of a size which ensures a stable power unit during storage and handling, i.e. which ensures that the pre-strained torsion spring is not released prematurely if the power unit is subjected to shaking, jolting or other limited impacts.

The first engagement structure and the second engagement structure may be configured to engage via a releasable snap fit connection. For example, the first engagement structure may comprise a male connector comprising a head portion having a first transversal dimension and the second engagement structure may comprise a female connector comprising a transversally deflectable entrance section having an undeflected transversal dimension which is smaller than the first transversal dimension, and an accommodation section having a second transversal dimension which is at least as large as the first transversal dimension, allowing for reception and releasable retention of the head portion therein.

Hence, the power unit may be released within the housing by a simple axial force application to one of the first interface member and the second interface member which does not require visual access to the housing interior.

The first engagement structure may comprise an axially extending spline arranged on an exterior surface portion of the hollow body, and the axially expending spline may be configured to engage with a mating engagement structure on a receiving part of the drug delivery device, such as e.g. an interior surface of the housing. In particular, the axially extending spline may be configured for rotational interlocking engagement with the receiving part. A single geometry as the axially extending spline may thereby both serve to couple the first interface member to the second interface member and to couple the first interface member to e.g. the housing, simplifying the design of the power unit.

The hollow body may comprise a transversal end face adapted to abut a transversal interior surface of the receiving part, whereby the transversal interior surface defines an axial stop for the first interface member with respect to the receiving part, e.g. the housing.

In a second aspect of the invention a drug delivery device, such as a drug injection device, comprising a housing and a power unit as described above arranged in the housing is provided.

The drug delivery device may further comprise a piston rod threadedly connected with the housing, and the first interface member may be rotationally locked with respect to the housing, while the second interface member may surround at least a portion of the piston rod and extend through the first interface member. Furthermore, the second interface member may be rotationally locked or restricted with respect to the piston rod, at least during dose expelling, and rotationally releasably locked with respect to the housing.

In one embodiment of the invention the second interface member comprises a tubular structure which is rotationally locked or restricted with respect to the piston rod distally of the hollow body and rotationally releasably locked with respect to the housing proximally of the hollow body.

In one embodiment of the invention the second interface member is a drive tube which is, or is adapted to be, rotationally locked or restricted with respect to the piston rod via a rotatable piston rod guide member.

In one embodiment of the invention the second interface member is a drive tube having a toothed exterior surface portion which is rotationally releasably locked with respect to the housing via a releasably retained gear wheel.

The housing may comprise an axially extending body having a radially inwardly directed surface and a housing engagement structure on the radially inwardly directed surface. The first engagement structure may comprise an axially extending spline on an exterior surface portion of the hollow body which axially extending spline may be engaged with the housing engagement structure to thereby rotationally lock the first interface member with respect to the housing.

The housing may further comprise a transversal interior surface defining an axial stop for, and a mounted position of, the first interface member in the housing, and the first interface member and the second interface member may be adapted to undergo the relative motion from the first relative axial position to the second relative axial position by axial movement of the second interface member relative to the housing, when the first interface member is in the mounted position.

In one embodiment of the invention the second end portion of the torsion spring is arranged between the skirt and a portion of the tubular structure covered by the skirt. Further, the second engagement structure forms part of the skirt and engages with the first engagement structure in the first relative axial position of the first interface member and the second interface member such that the skirt and the hollow body together cover the torsion spring.

The drug delivery device may further comprise a second piston rod threadedly connected with the housing and arranged in parallel with the piston rod, and the second interface member may be rotationally coupled with an intermediate structure, which intermediate structure is rotationally releasably locked with respect to the housing and further rotationally coupled with the second piston rod.

In one embodiment of the invention the intermediate structure comprises a gear wheel which is rotationally coupled with the second piston rod via a second drive tube arranged in parallel with the second interface member. The second drive tube may be rotationally locked or restricted with respect to the second piston rod via a second rotatable piston rod guide member.

In a third aspect the invention provides a method of pre-straining a torsion spring for a drug delivery device. The method comprises: (i) prior to insertion in a housing of the drug delivery device, attaching a first end of the torsion spring to an interior surface of a hollow body of a first interface member extending along a reference axis, the first interface member comprising a first engagement structure, (ii) prior to, simultaneously with, or subsequent to step (i) attaching a second end of the torsion spring to a second interface member comprising a tubular structure adapted to extend at least partially through the hollow body, a skirt on the tubular structure, and a second engagement structure, (iii) inducing a relative rotational motion about the reference axis between the first interface member and the second interface member, thereby bringing the torsion spring to a twisted state, and (iv) bringing the first interface member and the second interface member to a relative axial position in which the first engagement structure and the second engagement structure are engaged, thereby securing the torsion spring in the twisted state, wherein in the relative axial position of the first interface member and the second interface member the torsion spring is accommodated in a user inaccessible space defined by the hollow body and the skirt The method thus provides a power unit which can be assembled prior to assembly of the drug delivery device and stored separately, in a secure manner, as a sub-assembly unit.

Step (iii) may comprise aligning the first interface member and the second interface member angularly such that the first engagement structure and the second engagement structure face one another along the reference axis, and step (iv) may accordingly comprise bringing the first interface member and the second interface member to the relative axial position solely by converging relative axial motion. This provides for particularly simple movement patterns in the assembly process.

If the second engagement structure forms part of the skirt and comprises a male or female part of a snap fit coupling, and the first engagement structure comprises a mating female or male part, step (iv) leads to the first interface member and the second interface member being rotationally interlocked by means of a releasable snap fit connection.

In a fourth aspect the invention provides a method of mounting a power unit in a housing of a drug delivery device, the power unit comprising a first interface member having a first engagement structure, a second interface member having a second engagement structure, and a pre-strained torsion spring comprising a first end portion being attached to the first interface member and a second end portion being attached to the second interface member, the torsion spring being pre-strained to apply a torque for inducing a relative rotational motion between the first interface member and the second interface member, the method comprising: (i) inserting the power unit, while in a first state in which the first engagement structure and the second engagement structure are engaged to prevent the relative rotational motion between the first interface member and the second interface member, into the housing along a reference axis until the first interface member meets an axial stop, (ii) introducing a relative motion along the reference axis between the first interface member and the second interface member by urging the second interface member further into the housing along the reference axis, thereby bringing the power unit to a second state in which the first engagement structure and the second engagement structure are disengaged, and (iii) prior to the power unit reaching the second state rotationally releasably locking or restricting the second interface member with respect to the housing.

The drug delivery device may comprise a piston rod threadedly engaged with the housing, and step (i) may be carried out by mounting, e.g. sliding, a portion of the power unit along or over a portion of the piston rod.

Step (ii) may be carried out by moving the second interface member translationally and/or helically with respect to the housing a predetermined axial distance, or an axial distance lying within a predetermined interval, e.g. until the second interface member meets a second axial stop.

Step (iii) ensures that when the power unit is fully mounted in the housing and the first engagement structure and the second engagement structure are disengaged the torsion spring remains in its pre-strained condition, i.e. the torsion spring will not automatically unwind as a result of the power unit being brought to the second state.

In a fifth aspect of the invention a drug delivery device is provided comprising a housing, a first piston rod threadedly connected with the housing, a second piston rod threadedly connected with the housing, a power unit as described in the above in connection with the first aspect of the invention arranged about at least a portion of the first piston rod, where the first interface member is rotationally locked with respect to the housing, and the second interface member is rotationally locked or restricted, or configured to be rotationally locked or restricted, with respect to the first piston rod, and a coupling mechanism rotationally coupling the second interface member and the second piston rod.

The drug delivery device may further comprise a drug reservoir holding portion holding, or adapted to receive and hold, a first reservoir carrying a first medical substance and a second reservoir carrying a second medical substance. The first reservoir may comprise a first cartridge sealed by a first piston, respectively a first penetrable septum, and the second reservoir may comprise a second cartridge sealed by a second penetrable septum, respectively a second piston.

The first piston rod and the second piston rod may be arranged parallel to one another along a housing axis which is parallel to the reference axis. In that case the drug reservoir holding portion may be adapted to hold the first reservoir and the second reservoir in correspondingly parallel orientations, distally of the first piston rod and the second piston rod such that the first piston is axially aligned with the first piston rod and the second piston is axially aligned with the second piston rod.

The first piston rod may comprise a first thread having a first pitch, and the second piston rod may comprise a second thread having a second pitch, the second pitch being different from the first pitch. In that case when the first piston rod and the second piston rod rotate together, as a consequence of the rotational coupling between the two provided by the power unit and the coupling mechanism, the axial travel of the second piston rod is different from the axial travel of the first piston rod. Hence, a zero-point adjustment of each dose expelling system must be made individually and independently of the other, entailing an individual manipulation of each piston rod. The fact that one power unit provides power to drive both piston rods and the power unit can be mounted over the first piston rod after concluded zero-point adjustment thereof implies that no torsion springs impede access to any of the piston rods during assembly, i.e. each piston rod can freely be advanced into initial abutment with the piston with which it is axially aligned.

In a sixth aspect of the invention a method of mounting a power unit in a drug delivery device housing is provided, the drug delivery device housing comprising a first nut member threadedly engaged with a first piston rod and a second nut member threadedly engaged with, or configured for threaded engagement with, a second piston rod, and the power unit comprising a first interface member having a first engagement structure, a second interface member having a second engagement structure, and a pre-strained torsion spring comprising a first end portion being attached to the first interface member and a second end portion being attached to the second interface member, the torsion spring being pre-strained to apply a torque for inducing a relative rotational motion between the first interface member and the second interface member about a reference axis, the method comprising (i) in a first state of the power unit in which the first engagement structure and the second engagement structure are engaged to prevent the relative rotational motion between the first interface member and the second interface member, sliding a portion of the power unit along or over a portion of the first piston rod until the first interface member meets an axial stop, (ii) introducing a relative motion along the reference axis between the first interface member and the second interface member by urging the second interface member distally into the drug delivery device housing, thereby bringing the power unit to a second state in which the first engagement structure and the second engagement structure are disengaged, and (iii) prior to the power unit reaching the second state rotationally releasably locking or restricting the second interface member with respect to the drug delivery device housing.

The second piston rod may be inserted into the drug delivery device housing and threadedly engaged with the second nut member prior to, simultaneously with, or subsequent to the insertion of the power unit into the drug delivery device housing.

In the present context, when the torsion spring is "accommodated in a user inaccessible space" this means that the torsion spring is, at least substantially, covered up and thereby not manipulable by the user. However, it does not imply that the space in which the torsion spring resides is hermetically sealed.

Further, in the present context, when a first entity is rotationally "locked" with respect to a second entity this implies a bi-directional rotational interlocking where no relative rotational motion between the first entity and the second entity can occur, whereas when a first entity is rotationally "restricted" with respect to a second entity this implies a unidirectional rotational interlocking where a relative rotational motion between the first entity and the second entity is allowed in one direction only, as e.g. in a ratchet mechanism. For example, if the second interface member is rotationally restricted with respect to the housing then rotation of the second interface member in one direction relative to the housing is prevented. In the specific case the one direction will correspond to the rotational direction for the second spring end during unwinding of the pre-strained torsion spring. Finally, when two entities are rotationally "coupled" this simply implies that a rotation of the one causes some rotation of the other.

For the avoidance of any doubt, in the present context the term "medical substance" designates a medium which is used in the treatment, prevention or diagnosis of a condition, i.e. including a medium having a therapeutic or metabolic effect in the body. Further, the terms "distal" and "proximal" denote positions at or directions along a drug delivery device, or a needle unit, where "distal" refers to the drug outlet end and "proximal" refers to the end opposite the drug outlet end.

In the present specification, reference to a certain aspect or a certain embodiment (e.g. "an aspect", "a first aspect", "one embodiment", "an exemplary embodiment", or the like) signifies that a particular feature, structure, or characteristic described in connection with the respective aspect or embodiment is included in, or inherent of, at least that one aspect or embodiment of the invention, but not necessarily in/of all aspects or embodiments of the invention. It is emphasized, however, that any combination of the various features, structures and/or characteristics described in relation to the invention is encompassed by the invention unless expressly stated herein or clearly contradicted by context.

The use of any and all examples, or exemplary language (e.g., such as, etc.), in the text is intended to merely illuminate the invention and does not pose a limitation on the scope of the same, unless otherwise claimed. Further, no language or wording in the specification should be construed as indicating any non-claimed element as essential to the practice of the invention.

BRIEF DESCRIPTION OF THE DRAWINGS

In the following the invention will be further described with references to the drawings, wherein FIG. 5 is a longitudinal section view of a proximal portion of the power unit in the engaged state after insertion into the drug delivery device housing, FIG. 6 is a longitudinal section view of a proximal portion of the power unit in the disengaged state in the drug delivery device housing.

In the figures like structures are mainly identified by like reference numerals.

DESCRIPTION OF EXEMPLARY EMBODIMENTS

When/If relative expressions, such as "upper" and "lower", "left" and "right", "horizontal" and "vertical", "clockwise" and "counter-clockwise", etc., are used in the following, these refer to the appended figures and not necessarily to an actual situation of use. The shown figures are schematic representations for which reason the configuration of the different structures as well as their relative dimensions are intended to serve illustrative purposes only.

Figure 1:
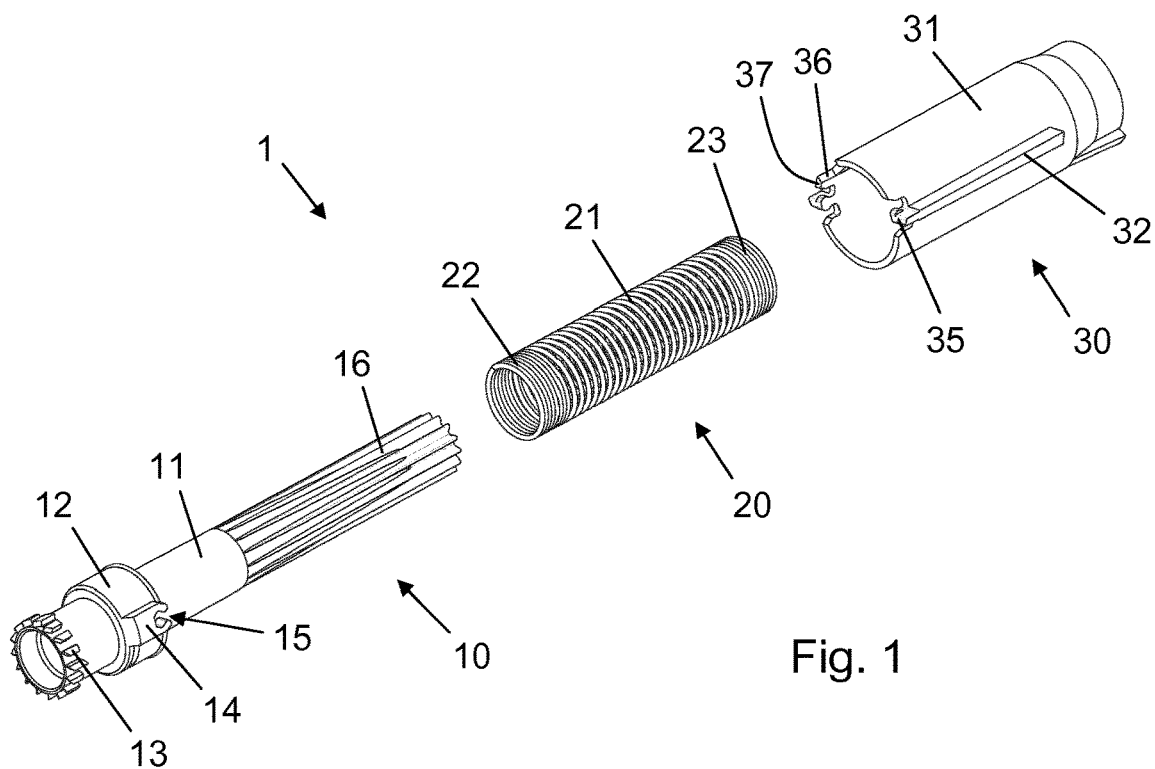
FIG. 1 is an exploded perspective view of a power unit according to an embodiment of the invention.

FIG. 1 is an exploded perspective view of a sub-assembly according to an embodiment of the invention in the form of a power unit 1. The power unit 1 is configured for use in a drug delivery device, such as e.g. an injection device, to supply energy to execute a dose expelling action. In the present exemplary embodiment the power unit 1 comprises a drive tube 10, a spring base 30, and a torsion spring 20 arranged to act between the drive tube 10 and the spring base 30 to provide a rotational bias.

The drive tube 10 has a tubular body 11 which is provided with a circumferentially corrugated section 16 at a proximal end portion and an exterior toothing 13 at a distal end portion. A skirt 12 is formed on the tubular body 11 near the exterior toothing 13 and carries a pair of catch structures 14 (only one is visible), each defining a receiving space 15.

The spring base 30 has a tubular spring base body 31 with a pair of axially extending splines 32 formed on its exterior surface. A coupling head 35 is provided at the distal end of each spline 32. The coupling head 35 has a shape which corresponds with the receiving space 15. At its distal end the spring base body 31 further has an axial protrusion 36 with a transversal end face 37.

The torsion spring 20 is a coil spring having a spring body 21 which extends between a distal spring end 22 and a proximal spring end 23. The distal spring end 22 is configured to be received by, and rotationally fixed in, the skirt 12, whereas the proximal spring end 23 is configured to be received by, and rotationally fixed in, the spring base body 31.

Figure 2:
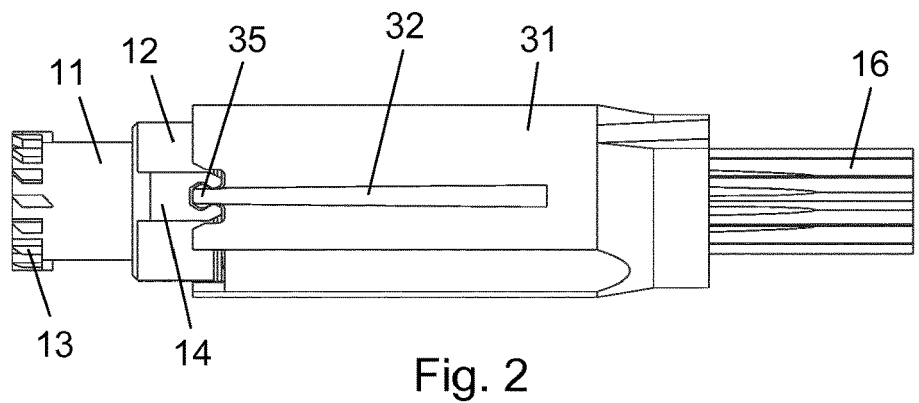
FIG. 2 is a side view of the power unit in an engaged state.

FIG. 2 is a side view of the power unit 1 in an engaged state, where the coupling head 35 occupies the receiving space 15. The torsion spring 20 is pre-twisted to provide a rotational bias of the drive tube 10 relative to the spring base 30 and retained by the rotational interlocking connection established by the engagement between the spline 32 and the catch structure 14. The particular relative angular displacement of the distal spring end 22 and the proximal spring end 23 introduced in the course of the pre-twisting of the torsion spring 20 is predetermined in accordance with the intended exemplary use of the power unit 1 in a dual cartridge injection device, where it is required to provide energy for two parallel dose engines.

Figure 3:
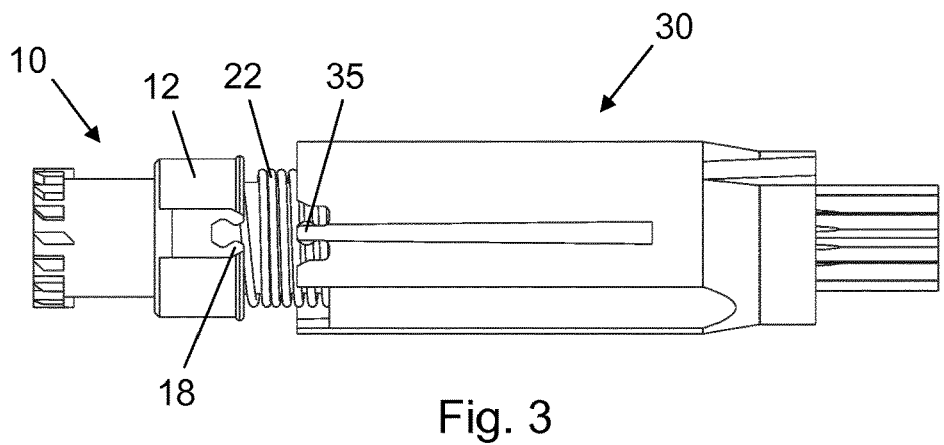
FIG. 3 is a side view of the power unit in a disengaged state.

As indicated in FIG. 3 the catch structure 14 has a pair of inwardly inclined fingers 18 which contribute to defining the receiving space 15 and which are elastically supported to thereby provide a snap fit engagement with the coupling head 35. The fingers 18 are dimensioned such that a predetermined axial release force is required in order to separate the spring base 30 and the drive tube 10.

In FIG. 3 the power unit 1 is in a disengaged state in which the coupling head 35 has been pulled out of the receiving space 15, exposing the distal spring end 22 to the surroundings. In the disengaged state the torsion spring 20 is released and will introduce a relative rotational motion between the drive tube 10 and the spring base 30, unless the spring base 30 and the drive tube 10 are prevented from relative rotation by other interactions, as will be explained in more detail below.

Figure 4:
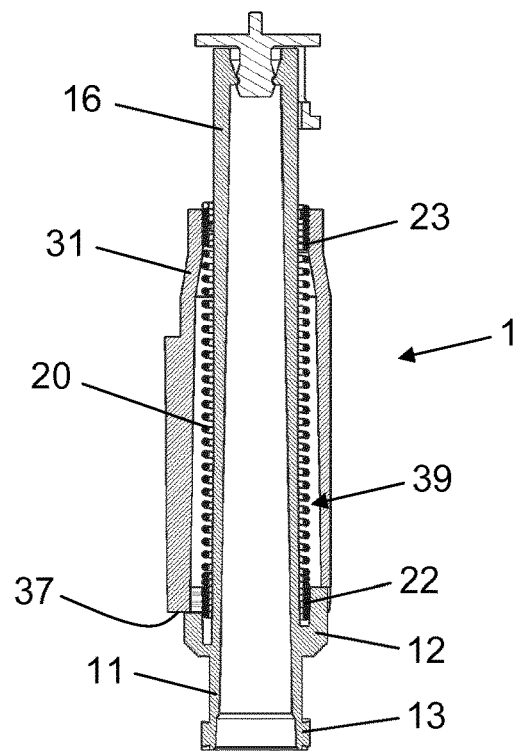
FIG. 4 is a longitudinal section view of the power unit during mounting in a drug delivery device housing.
Figure 4:
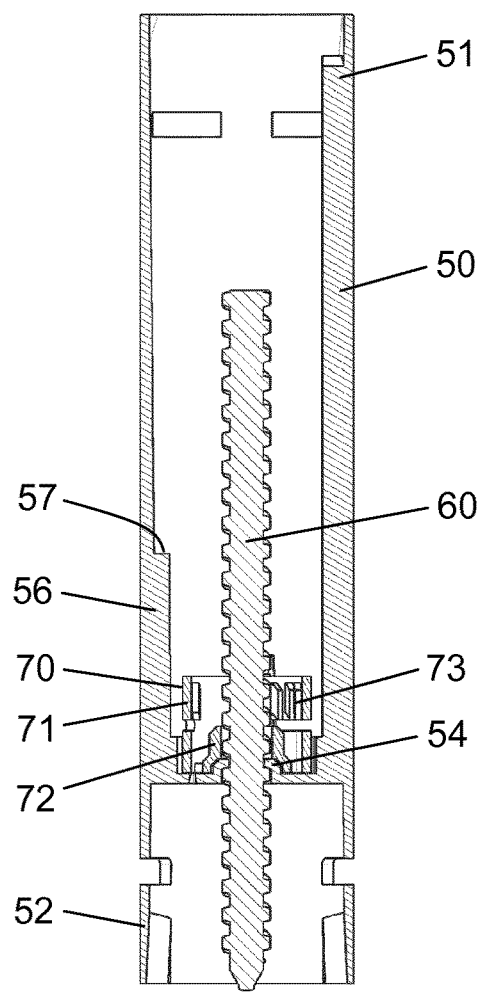

FIG. 4 is a longitudinal section view showing the power unit 1 just before mounting in a housing 50 of the dual cartridge injection device. In this particular sectional view one of the dose engines is hidden. The housing 50 extends between a proximal end portion 51, which is a user operable end portion, and a distal end portion 52 which is configured to receive and retain a drug cartridge (not shown). An integral nut member 54 is formed near the distal end portion 52 and is configured to engage with a threaded piston rod 60. The piston rod 60 has a non-circular cross-section and is by geometry rotationally interlocked with a piston rod interfacing portion 72 of a piston rod driver 70. A pure rotation of the piston rod driver 70 will thus cause a rotation of the piston rod 60 which will be converted to a helical displacement of the piston rod 60 relative to the housing 50 due to the threaded connection with the nut member 54. A helical displacement of the piston rod 60 will cause an advancement of a piston (not shown) in the drug cartridge and will thereby lead to an expelling of drug therefrom. The piston rod driver 70 further comprises a drive tube interfacing portion 71 carrying an interior toothing 73 for axially sliding reception of the exterior toothing 13.

The housing 50 has an axial ridge 56 along an interior surface portion, the end of the axial ridge 56 forming a radial shelf 57.

It is noted that in the engaged state of the power unit 1 the torsion spring 20 is completely shielded from the outside and thus secured in a user inaccessible space 39 between the tubular body 11 and the spring base body 31. The power unit 1 can thus be handled by a user, or a machine, with a minimum risk of the torsion spring 20 being prematurely released and/or the spring coils entangling.

Mounting of the power unit 1 in the housing 50 is carried out in two steps. Initially, the entire power unit 1 is axially slid into the interior of the housing 50, over the piston rod 60, until the end face 37 abuts the shelf 57 which prevents further distal movement of the spring base 30. During the insertion of the power unit 1 the splines 32 respectively engage interior axial tracks (not visible) in housing 50, rotationally fixing the spring base 30 with respect to the housing 50, and the corrugated section 16 slidably engages a clutch 80 (see FIG. 7) which in an idle state of the dual cartridge injection device is rotationally locked with respect to the housing 50. FIG. 5 shows the position of the power unit 1 in the housing 50 at the end of the initial mounting step. In this position the power unit 1 is still in the engaged state.

The second mounting step comprises applying a distally directed force to the drive tube 10. Resultantly, while the spring base 30 sits at the shelf 57 the drive tube 10 is urged further distally into the housing 50, as illustrated in FIG. 6. By this force application to the drive tube 10 the coupling head 35 is pulled out of the receiving space 15 and the power unit 1 is thus shifted to the disengaged state, but at the same time the corrugated section 16 merely slides along the clutch 80, maintaining engagement therewith. Hence, as the clutch 80 is rotationally locked with respect to the housing 50 the drive tube 10 is prevented from rotating, and the torsion spring 20 is still retained in its pre-twisted state.

During the second mounting step the drive tube 10 is brought to an idle state position within the housing 50 where the exterior toothing 13 has slid past the interior toothing 73 and resides close to the nut member 54. The power unit 1 is now fully mounted in the housing 50, notably without having affected the previously mounted piston rod 60.

Figure 7:
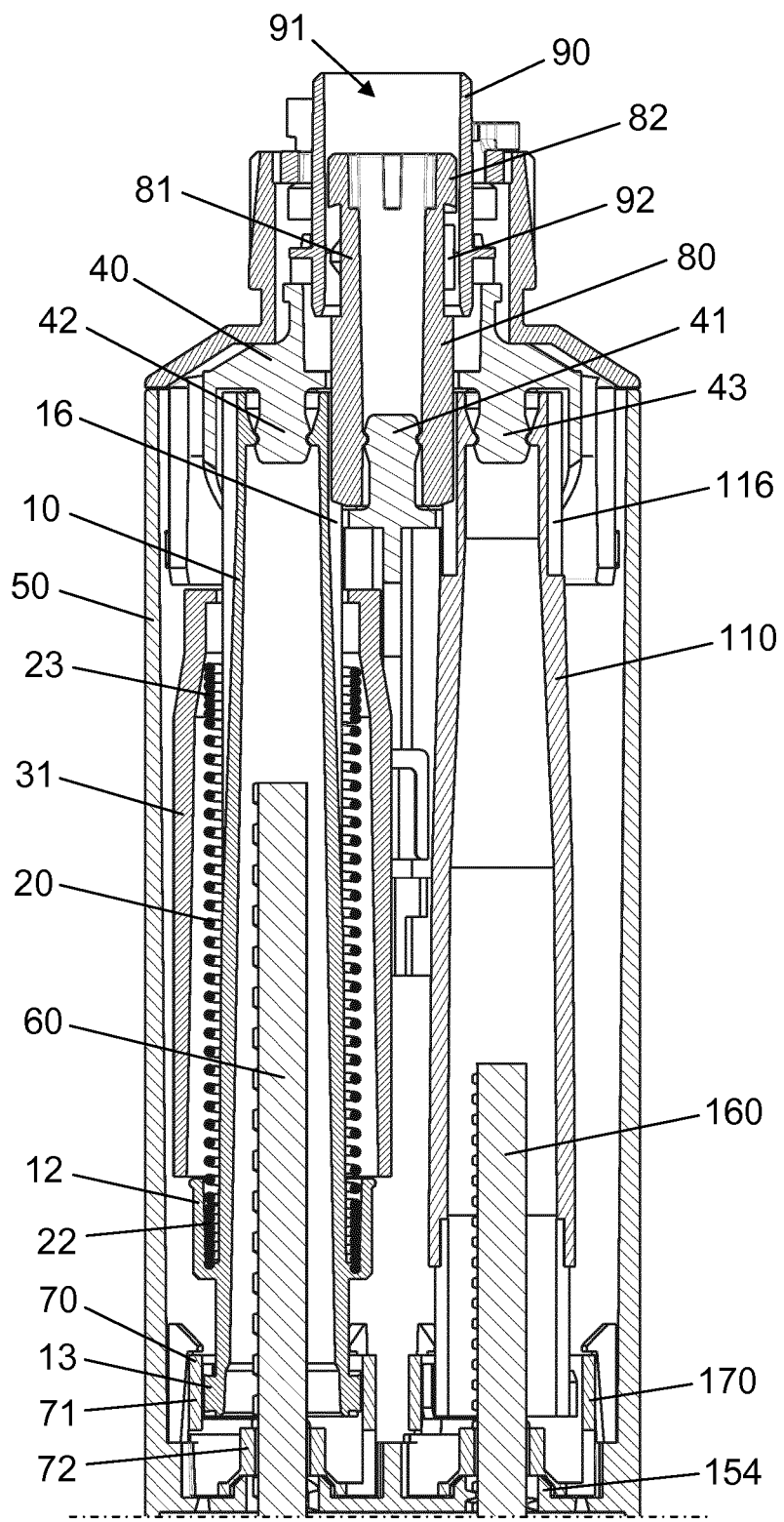
FIG. 7 is a longitudinal section view of a proximal portion of the drug delivery device including the power unit in an intermediate state during dose expelling.

FIG. 7 is a longitudinal section view of a proximal portion of the dual cartridge injection device in a plane orthogonal to the section plane of FIGS. 4-6. As can be seen the device comprises two parallel dose engines, one to the left including the power unit 1 and one to the right. The dose engine to the right has a piston rod 160 arranged in threaded engagement with a nut member 154 formed in the housing 50, a rotatable piston rod driver 170, and a drive tube 110 with a circumferentially corrugated section 116, similarly to the dose engine to the left. The corrugated section 116 is engaged with the clutch 80 in a manner similar to the corrugated section 16 of the drive tube 10.

The clutch 80 comprises a neck 81 and a toothed head 82 slidably arranged in an interior space 91 of a top base 90 which is rotationally fixed with respect to the housing 50. The top base 90 has an interior axial ridge 92 which in the idle state of the dual cartridge injection device (not the one shown in FIG. 7) engages with the toothed head 82 to prevent rotational motion of the clutch 80 relative to the top base 90.

The dual cartridge injection device is a distally triggered device in the sense that a needle insertion movement of the device against the skin of the user causes a proximal displacement of an axial rod (not visible) within the housing 50 against the force of a rod spring (not visible). The axial rod is connected to a rear activator 40 such that a proximal displacement of the axial rod relative to the housing 50 causes a proximal displacement of the rear activator 40 and a distal displacement of the axial rod relative to the housing 50 causes a distal displacement of the rear activator 40.

The rear activator 40 comprises a central head 41 which is engaged with an interior protruding geometry in the clutch 80 to axially interlock the rear activator 40 and the clutch 80. The rear activator 40 further comprises a left side head 42 which is engaged with an interior protruding geometry in the drive tube 10 to axially interlock the rear activator 40 and the drive tube 10, and a right side head 43 which is engaged with an interior protruding geometry in the drive tube 110 to axially interlock the rear activator 40 and the drive tube 110.

In FIG. 7 the dual cartridge injection device is shown in a drug expelling state, i.e. following a depression of the device against the skin of the user for insertion of an attached injection needle (not shown). The needle insertion movement has caused a proximal displacement of the axial rod and thereby of the rear activator 40. Due to the above described respective axial connections the proximal displacement of the rear activator 40 has caused corresponding proximal displacements of the clutch 80 and the two drive tubes 10, 110. This has resulted firstly in the exterior toothing 13 of the drive tube 10 sliding into engagement with the interior toothing 73 of the piston rod driver 70 and a similar rotational connection being established between the drive tube 110 and the piston rod driver 170, and secondly in the toothed head 82 sliding out of engagement with the interior axial ridge 92. The actual disengagement of the toothed head 82 from the interior axial ridge 92 occurs simultaneously with or subsequently to the engagement of the exterior toothing 13 with the interior toothing 73.

When the toothed head 82 is disengaged from the interior axial ridge 92 the clutch 80 is no longer rotationally fixed and the torsion spring 20 is therefore free to unwind and release its stored energy, the power unit 1 being in the disengaged state. Since the spring base 30 is rotationally fixed with respect to the housing 50 the unwinding of the torsion spring 20 causes a rotational motion of the drive tube 10, and thereby of the piston rod driver 70 due to the rotational engagement between the exterior toothing 13 and the interior toothing 73. The piston rod interfacing portion 72, being rotationally interlocked with the piston rod 60, causes a corresponding angular displacement of the piston rod 60 which therefore travels helically though the nut member 54 and advances a piston in a first drug containing cartridge (not shown).

Meanwhile, the rotation of the drive tube 10 and the engagement between the corrugated section 16 and the clutch 80 result in a rotational motion of the clutch 80. The rotation of the clutch 80 induces a rotation of the drive tube 110 due to the engagement between the clutch 80 and the corrugated section 116, and eventually results in a helical displacement of the piston rod 160 through the nut member 154 and thereby of an advancement of a piston in a second drug containing cartridge (not shown). A single power unit 1 is thus used to provide energy for driving both piston rods 60, 160, making the assembly process easier and the device as a whole less expensive to produce.

When the injection process is completed and the injection needle is retracted from the skin the axial rod and the rear activator 40 will return to their respective idle state axial positions, slaving the clutch 80 and the two drive tubes 10, 110 distally relative to the housing 50, whereby the toothed head 82 slides into engagement with the interior axial ridge 92 and locks the clutch 80 rotationally to the housing 50, the drive tube 10 disengages from the piston rod driver 70, and the drive tube 110 disengages from the piston rod driver 170. The power unit 1 is still in the disengaged state.

The dual cartridge injection device may be a single use type of device intended for discarding following a completed injection process or a multi-use type of device capable of delivering multiple respective doses of the two drugs. In either case the torsion spring 20 may be dimensioned and pre-twisted to store sufficient energy to advance both pistons to the end of, or to a desired position within, their respective cartridges. In case of a multi-use type of device, a dose defining mechanism may be incorporated to provide for release of the torsion spring energy in portions.

The invention claimed is:

1. A power unit for a drug delivery device, comprising:
   a first interface member extending along a reference axis and comprising a hollow body and a first engagement structure,
   a second interface member comprising a tubular structure extending at least partially through the hollow body and having a skirt, and a second engagement structure configured for releasable engagement with the first engagement structure, and
   a torsion spring comprising a first end portion being attached to the first interface member and a second end portion being attached to the second interface member, the torsion spring being pre-strained to induce a relative rotational motion between the first interface member and the second interface member,
   wherein the first interface member and the second interface member are configured for relative motion along the reference axis from a first relative axial position in which the first engagement structure and the second engagement structure are engaged to prevent the relative rotational motion between the first interface member and the second interface member to a second relative axial position in which the first engagement structure and the second engagement structure are disengaged, and
   wherein in the first relative axial position of the first interface member and the second interface member the torsion spring is accommodated in a user inaccessible space defined by the hollow body and the skirt.

2. A power unit according to claim 1, wherein in the first relative axial position of the first interface member and the second interface member the first engagement structure and the second engagement structure are further engaged to obstruct the relative axial motion between the first interface member and the second interface member.

3. A power unit according to claim 2, wherein in the first relative axial position of the first interface member and the second interface member the first engagement structure and the second engagement structure are engaged via a releasable snap fit connection.

4. A power unit according to claim 1, wherein the second end portion is positioned between the skirt and a portion of the tubular structure covered by the skirt, and wherein the second engagement structure forms part of the skirt.

5. A power unit according to claim 1, wherein the first engagement structure comprises an axially extending spline arranged on an exterior surface portion of the hollow body and configured for rotational interlocking engagement with a mating structure on a receiving part of the drug delivery device.

6. A power unit according to claim 1, wherein the hollow body comprises a transversal end face adapted to abut a transversal interior surface of the receiving part, the transversal interior surface thereby defining a stop for axial travel of the first interface member relative to the receiving part.

7. A drug delivery device comprising a housing and a power unit according to claim 1 arranged in the housing.

8. A drug delivery device according to claim 7, further comprising a piston rod threadedly connected with the housing, wherein the hollow body is rotationally locked with respect to the housing, and wherein the tubular structure surrounds at least a portion of the piston rod and is rotationally locked or restricted with respect to the piston rod, at least during dose expelling, and rotationally releasably locked with respect to the housing.

9. A drug delivery device according to claim 8, wherein the tubular structure is rotationally locked with respect to the piston rod distally of the hollow body and rotationally releasably locked with respect to the housing proximally of the hollow body.

10. A drug delivery device according to claim 8, wherein the housing comprises a housing engagement structure on a radially inwardly directed axially extending surface, and the first engagement structure comprises an axially extending spline arranged on an exterior surface portion of the hollow body, and wherein the axially extending spline is engaged with the housing engagement structure.

11. A drug delivery device according to claim 10, wherein the housing further comprises a transversal interior surface defining an axial stop for, and a mounted position of, the first interface member in the housing, and wherein the first interface member and the second interface member are adapted to undergo the relative motion from the first relative axial position to the second relative axial position by axial movement of the second interface member relative to the housing, when the first interface member is in the mounted position.

12. A drug delivery device according to claim 7, further comprising a second piston rod threadedly connected with the housing and arranged in parallel with the piston rod, wherein the second interface member is rotationally coupled with an intermediate structure, which intermediate structure is rotationally releasably locked with respect to the housing and further rotationally coupled with the second piston rod.

13. A method of pre-straining a torsion spring for a drug delivery device, comprising:
   (i) prior to insertion in a housing of the drug delivery device, attaching a first end portion of the torsion spring to an interior surface of a hollow body of a first interface member extending along a reference axis, the first interface member comprising a first engagement structure,
   (ii) attaching a second end portion of the torsion spring to a second interface member comprising a tubular structure adapted to extend at least partially through the hollow body, a skirt on the tubular structure, and a second engagement structure,
   (iii) inducing a relative rotational motion about the reference axis between the first interface member and the second interface member, thereby bringing the torsion spring to a twisted state, and
   (iv) bringing the first interface member and the second interface member to a relative axial position in which the first engagement structure and the second engagement structure are engaged, thereby securing the torsion spring in the twisted state,
   wherein in the relative axial position of the first interface member and the second interface member the torsion spring is accommodated in a user inaccessible space defined by the hollow body and the skirt.

14. A method according to claim 13, wherein step (iii) comprises aligning the first interface member and the second interface member angularly such that the first engagement structure and the second engagement structure face one another along the reference axis, and wherein step (iv) comprises bringing the first interface member and the second interface member to the relative axial position solely by converging relative axial motion.

15. A method of mounting a power unit in a drug delivery device housing, the power unit comprising a first interface member comprising a first engagement structure, a second interface member comprising a second engagement structure, and a torsion spring comprising a first end portion being attached to the first interface member and a second end portion being attached to the second interface member, the torsion spring being pre-strained to apply a torque for inducing a relative rotational motion between the first interface member and the second interface member, the method comprising:
- (i) inserting the power unit, while in a first state in which the first engagement structure and the second engagement structure are engaged to prevent the relative rotational motion between the first interface member and the second interface member, into the drug delivery device housing along a reference axis until the first interface member meets an axial stop,
- (ii) introducing a relative motion along the reference axis between the first interface member and the second interface member by urging the second interface member further into the drug delivery device housing along the reference axis, thereby bringing the power unit to a second state in which the first engagement structure and the second engagement structure are disengaged, and
- (iii) prior to the power unit reaching the second state rotationally releasably locking or restricting the second interface structure relative to the drug delivery device housing.

* * * * *